United States Patent [19]

Hickey et al.

[11] Patent Number: 5,763,714
[45] Date of Patent: Jun. 9, 1998

[54] PROCESS AND APPARATUS FOR THE PRODUCTION AND RECOVERY OF P-XYLENE

[75] Inventors: Thomas P. Hickey; Dennis Hearn; Hugh M. Putman, all of Houston, Tex.

[73] Assignee: Catalytic Distillation Technologies, Pasadena, Tex.

[21] Appl. No.: 780,254

[22] Filed: Jan. 8, 1997

Related U.S. Application Data

[60] Provisional application No. 60/010,182, Jan. 18, 1996.

[51] Int. Cl.$^6$ .............................. C07C 5/22; C07C 7/04; C07C 7/13; B01D 3/34
[52] U.S. Cl. .............. 585/253; 585/258; 585/478; 585/805; 585/807; 585/820; 585/828; 203/28; 203/29; 203/DIG. 6
[58] Field of Search ................... 585/253, 264, 585/319, 258, 477, 478, 805, 807, 820, 828; 203/28, 29, DIG. 6

[56] References Cited

U.S. PATENT DOCUMENTS

| | | | |
|---|---|---|---|
| 3,715,406 | 2/1973 | Brown et al. | 260/669 |
| 3,856,871 | 12/1974 | Haag et al. | 260/668 |
| 3,948,758 | 4/1976 | Bonacci et al. | 208/92 |
| 3,957,621 | 5/1976 | Bonacci et al. | 208/60 |
| 4,007,231 | 2/1977 | Butter | 260/672 |
| 4,038,334 | 7/1977 | Wood | 260/671 |
| 4,067,919 | 1/1978 | Butter | 260/668 |
| 4,080,396 | 3/1978 | Butter | 260/673 |
| 4,101,595 | 7/1978 | Chen et al. | 260/668 |
| 4,118,429 | 10/1978 | Fritsch et al. | 260/674 SA |
| 4,127,471 | 11/1978 | Suggitt et al. | 208/60 |
| 4,171,290 | 10/1979 | Mieville | 252/466 |
| 4,319,067 | 3/1982 | Kreeger | 585/459 |
| 4,361,713 | 11/1982 | Kaeding | 585/467 |
| 4,439,350 | 3/1984 | Jones, Jr. | 502/527 |
| 4,443,559 | 4/1984 | Smith, Jr. | 502/527 |
| 4,721,827 | 1/1988 | Cullo et al. | 585/467 |
| 4,761,514 | 8/1988 | Menard | 585/475 |
| 4,849,569 | 7/1989 | Smith, Jr. | 585/446 |
| 4,891,458 | 1/1990 | Innes et al. | 585/323 |
| 5,030,786 | 7/1991 | Shamshoum et al. | 585/467 |
| 5,240,892 | 8/1993 | Klocke | 502/77 |
| 5,464,799 | 11/1995 | Casci et al. | 502/65 |
| 5,476,978 | 12/1995 | Smith, Jr. et al. | 585/323 |

*Primary Examiner*—Glenn Caldarola
*Assistant Examiner*—Thuan D. Dang
*Attorney, Agent, or Firm*—Kenneth H. Johnson

[57] ABSTRACT

A mixed aromatic stream is hydrotreated to remove olefins and fractionated to separate $C_9+$ heavies in a distillation column reactor and the $C_8$ and lighter material is fed to a selective adsorption unit where the para-xylene is removed. The para-xylene depleted raffinate therefrom may be subjected to isomerization to form additional para-xylene. The effluent from the isomerization can be fed to the distillation column reactor for hydrogenation of any olefins formed during the isomerization or directly to the adsorption unit.

13 Claims, 1 Drawing Sheet

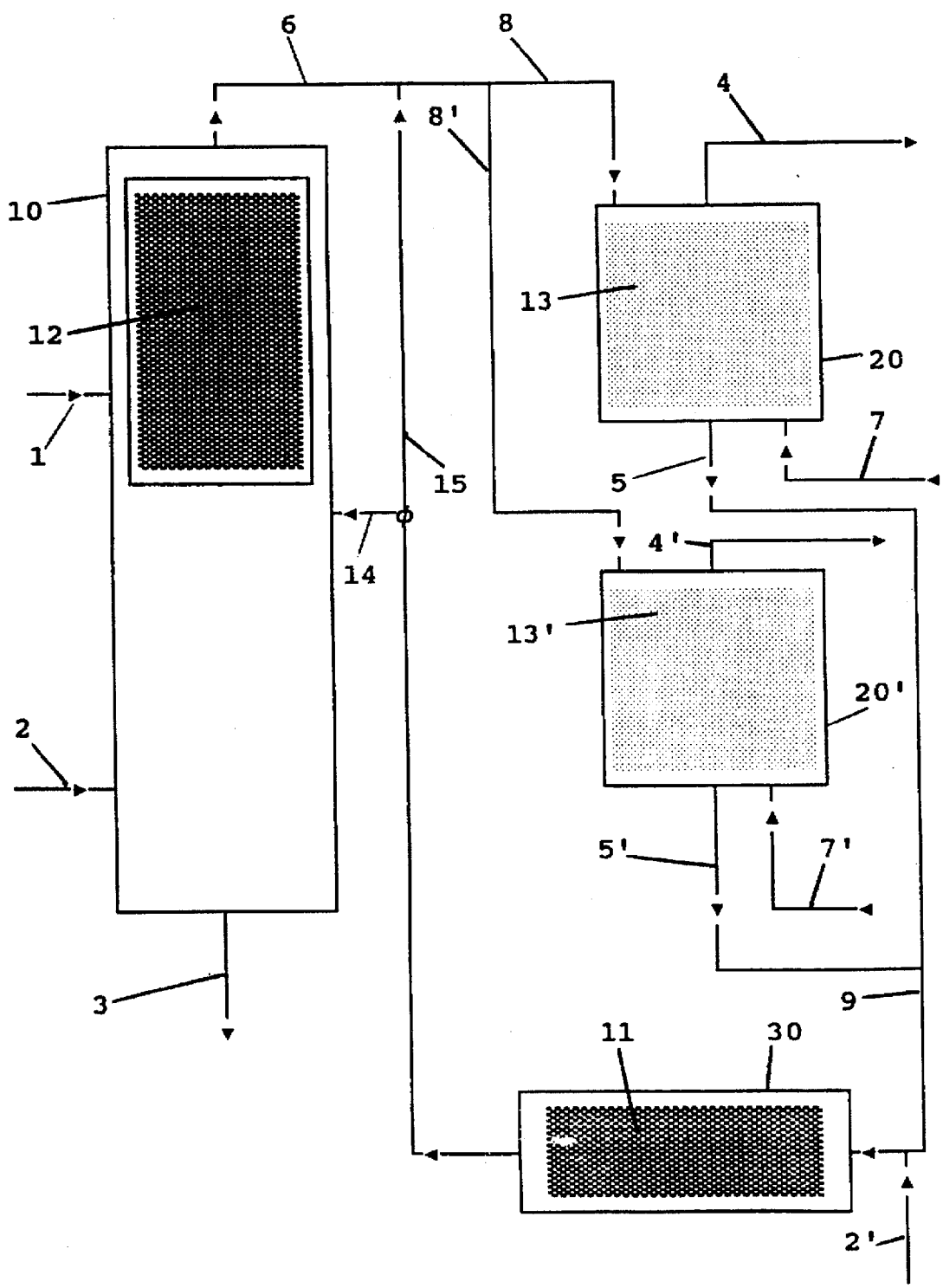

1

PROCESS AND APPARATUS FOR THE PRODUCTION AND RECOVERY OF P-XYLENE

BACKGROUND OF THE INVENTION

1. Field of the Invention

The present invention relates to the recovery of p-xylene from mixed aromatic streams. More particularly the invention relates to a process wherein p-xylene is recovered from a mixed aromatic stream by selective hydrogenation to remove olefins followed by selective adsorption of the p-xylene.

2. Related Art

Para-xylene (p-xylene) is an important chemical because of its usage in the production of terephthalic acid which in turn has many uses in the production of synthetic resins and fibers, vitamins and other pharmaceutical syntheses. Para-xylene is generally contained in a mixed aromatic stream which has been separated from petroleum naphthas, primarily reformates or pyrolysis distillates, by solvent extraction. Regardless of the method by which the p-xylene is produced, the product effluent is a mixture of orthoxylene (o-xylene), meta-xylene (m-xylene), p-xylene and ethylbenzene. Generally the proportions approximate 50.0% m-xylene, 20.0% p-xylene, 20.0% o-xylene and 10.0% ethylbenzene.

The ethylbenzene may be separated by fractional distillation, although this may be costly. In the past the p-xylene has been separated by fractional crystallization but the most common method now is by selective adsorption in a mole sieve as more particularly described below. Such a process and earlier background is disclosed in U.S. Pat. No. 3,895,080. Further disclosure of adsorbent separation of p-xylene is contained in U.S. Pat. No. 3,943,184.

U.S. Pat. No. 5,431,888 discloses a multi-purpose distillation column reactor wherein a hydrogenation catalyst for hydrotreating an isoolefin containing light naphtha from a fluid catalytic cracking unit to remove diolefins and mercaptans is stacked below an etherification catalyst.

U.S. Pat No. 5,087,780 to Arganbright disclosed a process for the hydroisomerization of butenes using an alumina supported palladium oxide catalyst arranged in a structure for use as both the catalyst and distillation in a catalytic distillation reactor. The hydrogenation of dienes was also observed. PCT application WO 95/15934 discloses a process for the selective hydrogenation of the diolefins and acetylenic compounds in a olefin rich aliphatic hydrocarbon streams is disclosed wherein the selective hydrogenation is carried out at 40° to 300° F. under low hydrogen partial pressure in the range of about 0.1 psi to less than 70 psia at 0 to 350 psig in a distillation column reactor containing a hydrogenation catalyst which serves as a component of a distillation structure, such as supported PdO encased in tubular wire mesh.

Olefinic hydrocarbon impurities are commonly found in the aromatic containing hydrocarbon process streams such as those originating from reforming or steam cracking of naphthas. Alternatively, olefins can also be formed as by-products in a number of petrochemical processes, including the aforementioned isomerization. Removal of these olefins is important when the stream is to be separated by molecular sieves because the olefins will occupy sieve capacity and thereby adversely affect separation performance. One current practice for removing olefins involves the use of the clay treating process using selective adsorption wherein the hydrocarbon stream is contacted with a clay such as, activated bentonite, Attapulgus clay, fuller's earth, Superfiltrol, Floridin, and the like. These clays are composed primarily of amorphous and crystalline mixtures of silica and alumina, but are readily distinguishable from the structure and crystallinity of the crystalline aluminosilicate zeolites.

The $C_8$ aromatics have been isomerized to produce p-xylene using zeolites as in the Octafining process. The Octafining process and improvements thereon are discussed at length in U.S. Pat. No. 3,856,872.

U.S. Pat. No. 4,118,429 discloses a combined process for the production and recovery of p-xylene. The mixed aromatic stream is fed to a hydrotreater (if olefins are present) or straight to a distillation column to remove both the $C_7$ and lighter and $C_9$ and heavier material. The $C_8$'s are then fed to a mole sieve separation unit. The p-xylene depleted effluent from the separation unit is fed to an isomerization reactor wherein an equilibrium xylene mixture is produced. The effluent from the isomerization unit is then fed to the hydrotreater (along with the feed if it contains olefins) to remove the olefins. The effluent from the hydrotreater is then combined with the fresh feed to the mole sieve separation unit. Overall the reference presents a complicated integrated process.

SUMMARY OF THE INVENTION

The present invention is a process for recovering high purity p-xylene from mixed aromatic streams containing olefinic impurities comprising combining fractionation, hydrotreating in a single distillation column reactor wherein the $C_9$'s and heavies are removed as bottoms and the hydrotreated $C_8$ aromatics are removed as overheads for feed to a molecular sieve separation unit where the p-xylene is selectively adsorbed. The p-xylene depleted raffinate from the molecular sieve separation unit may be fed back into an isomerization reactor.

The adsorptive separation may be selected from any in the art but typically will utilize a type X and/or Y sieve to selectively adsorb the p-xylenes. The sieve is then contacted with a desorbent, such as toluene to displace the selectively adsorbed p-xylene.

BRIEF DESCRIPTION OF THE DRAWINGS

The figure is a flow diagram in schematic form of a preferred embodiment of the invention using catalytic distillation hydrogenation and fixed bed straight pass isomerization.

DESCRIPTION OF THE PREFERRED EMBODIMENT

The aromatic streams useful in the present invention may derive from any source. Generally the proportions approximate 50.0% m-xylene, 20.0% p-xylene, 20.0% o-xylene and 10.0% ethylbenzene. The olefinic impurities are usually present in amounts of less than 10,000 wppm, e.g. 5,000 to 7,000 wppm. The olefinic impurities are materials that boil in the range of aromatic fraction being processed for p-xylene recovery. These are for the most part hydrocarbons, and may include mono and poly unsaturations, such as butadienes, hexenes, heptenes, octenes, nonenes and the like.

The separation of p-xylene from mixed $C_8$ aromatic streams may be achieved by the selective adsorption utilizing either type X or type Y crystalline aluminosilicate zeolites as is well known in the art. These molecular sieve zeolites contain exchangeable cationic sites which, by way of ion-exchange, will be prepared to contain one or more metal cations from the group lithium, potassium, beryllium, magnesium, calcium, strontium, barium, nickel, copper, silver, manganese and cadmium. Generally, the cations of the metals from the Groups I-A and II-A have been preferred; a type X or type Y zeolite containing both potassium and barium is especially preferred.

Both liquid-phase and vapor-phase adsorptions may be utilized in the separation section of the present process. Liquid phase requires somewhat lower temperature levels which enhance the selectivity of the zeolite with respect to p-xylene. Typical adsorption-separation conditions include temperatures in the range of from about 100° F. to about 400° F. and pressures in the range of from atmospheric to about 500 psig. Suitable desorbents constitute those readily separated from the $C_8$ aromatic components, i.e., those having a different boiling range such that fractional distillation is feasible.

The adsorptions generally remove from 95 to 98 wt.% of the p-xylene, thus the stream returned to the isomerization reactor is predominately o- and m-xylene. Although the olefins were essentially completely saturated to alkanes from the feed to the adsorption unit, the isomerization may produce some olefins which are subsequently removed in the hydrogenation zone along with the olefins in the make-up feed.

The isomerization of the raffinate may be achieved with any number of currently available catalysts. Generally the catalysts used are also zeolites, but having a Group VIII noble metal component. In lieu of the zeolite the support may be an acidic alumina. Conditions for the isomerization include temperatures in the range of 650°–1000° F. and pressures of about 100 psig. Hydrogen is necessary to insure that the catalyst is active and is usually added in the range of about a 6.0:1 mole ratio of hydrogen to hydrocarbon. The isomerization can be carried out in a standard downflow fixed bed straight pass reactor.

While the isomerization may be carried out in a standard downflow reactor the hydrogenation is carried out in a distillation column reactor. The preferred catalyst is a "non-acidic" catalyst composite comprising a Group VIII noble metal component. The term "non-acidic" is used to connote that no intentional steps have been taken to provide an acid function such as the inclusion of silica or a halogen component. Typical catalysts contain from about 0.1 to 1.5% of the metal. The conditions within the hydrogenation zone are preferably between about 35 and 100 psig and between about 100° F. to 400° F. with an equivalent liquid hourly space velocity (volume of feed per volume of catalyst per hour) of between 2.5 and 10. The distillation column reactor is advantageously operated to separate the $C_9+$ heavier material from the feed stream before feeding to the selective adsorption separation unit. Hydrogen is added to keep the hydrogen to olefin mole ratio in the 1-10:1 range. Under these conditions the hydrogen partial pressure is less than 75 psia, more preferably less than 50 psia and generally in the range of 5 to 0.1 psia.

Broadly stated, the catalytic material is a component of a distillation system functioning as both a catalyst and distillation packing, i.e., a packing for a distillation column having both a distillation function and a catalytic function.

The reaction system can be described as heterogenous since the catalyst remains a distinct entity.

A preferred catalyst structure for the present hydrogenation or isomerization reactions comprises flexible, semi-rigid open mesh tubular material, such as stainless steel wire mesh, filled with a particulate catalytic material in one of several embodiments recently developed in conjunction with the present process.

One new catalyst structure developed for use in hydrogenations is described in U.S. Pat. No. 5,266,546 which is incorporated herein in its entirety. Briefly the new catalyst structure is a catalytic distillation structure comprising flexible, semi-rigid open mesh tubular material, such as stainless steel wire mesh, filled with a particulate catalytic material said tubular material having two ends and having a length in the range of from about one-half to twice the diameter of said tubular material, a first end being sealed together along a first axis to form a first seam and a second end being sealed together along a second axis to form a second seam wherein the plane of the first seam along the axis of said tubular material and the plane of the second seam along the axis of said tubular material bisect each other at an angle of about 15° to 90°.

U.S. Pat. Nos. 4,242,530 and 4,443,559 which are incorporated herein, disclose supported catalyst in a plurality of pockets in a cloth belt or wire mesh tubular structures, which is supported in the distillation column reactor by open mesh knitted stainless steel wire by twisting the two together into a helix. U.S. Pat. No. 5,348,710, which is incorporated herein, describes several other suitable structures in the prior art and discloses new structures suitable for this process. Other catalytic distillation structures useful for this purpose are disclosed in U.S. Pat. Nos. 4,731,229 and 5,073,236 which are also incorporated by reference.

The particulate catalyst material may be a powder, small irregular chunks or fragments, small beads and the like. The particular form of the catalytic material in the structure is not critical, so long as sufficient surface area is provided to allow a reasonable reaction rate. The sizing of catalyst particles can be best determined for each catalytic material (since the porosity or available internal surface area will vary for different material and of course affect the activity of the catalytic material).

For the present hydrogenations the preferred catalyst structures for the packing are those employing the more open structure of permeable plates or screen wire.

Hydrogenation is the reaction of hydrogen with a carbon-carbon multiple bond to "saturate" the compound. This reaction has long been known and is usually done at super atmospheric pressures and moderate temperatures using a large excess of hydrogen over a metal catalyst. Among the metals known to catalyze the hydrogenation reaction are platinum, rhenium, cobalt, molybdenum, nickel, tungsten and palladium. Generally, commercial forms of catalyst use supported oxides of these metals. The oxide is reduced to the active form either prior to use with a reducing agent or during use by the hydrogen in the feed. These metals also catalyze other reactions, most notably dehydrogenation at elevated temperatures. Additionally they can promote the reaction of olefinic compounds with themselves or other olefins to produce dimers or oligomers as residence time is increased.

Selective hydrogenation of hydrocarbon compounds has been known for quite some time. Peterson, et al in "The Selective Hydrogenation of Pyrolysis Gasoline" presented to the Petroleum Division of the American Chemical Society in September of 1962, discusses the selective hydrogenation of $C_4$ and higher diolefins. Boitiaux, et al in "Newest Hydrogenation Catalyst", *Hydrocarbon Processing*, March 1985, presents a general, non enabling overview of various uses of hydrogenation catalysts, including selective hydrogenation of a propylene rich stream and other cuts. Conventional liquid phase hydrogenations as presently practiced requires high hydrogen partial pressures, usually in excess of 200 psi and more frequently in a range of up to 400 psi or more. In a liquid phase hydrogenation the hydrogen partial pressure is essentially the system pressure.

The preferred hydrogenation catalyst is an alumina supported palladium catalyst having a palladium content of about 0.5 wt%. The hydrogenation catalyst is generally supplied in the form of small spheres or extrudates of from $\frac{1}{32}$ to $\frac{1}{4}$ inches in diameter. A preferred catalyst structure for the present hydrogenation reaction comprises flexible, semi-rigid open mesh tubular material, such as stainless steel wire mesh, filed with a particulate catalytic material in one of several embodiments recently developed in conjunction with the present process. Most particularly the structure described in U.S. Pat. No. 5,431,890 which is herein incorporated by reference is preferred for the hydrogenation catalyst structure. Disclosed therein is a bale shaped catalytic distillation structure formed by placing multiple link or continuous tube shaped structures on top of a wire mesh screen, such as demister wire, arrayed at an angle to the longitudinal axis of the bale, such that when the wire mesh screen is rolled up, the rolled structure provides a new and improved catalytic distillation structure. The tube comprises flexible, semi-rigid open mesh tubular element filled with a particulate catalytic material, the tube shaped structure having a fastener every 1–12 inches in length to form a multiple link.

The hydrogen stream at an effectuating hydrogen partial pressure of at least about 0.1 psia to less than 70 psia, preferably less than 50 psia is conveniently fed to the reaction distillation column along with the other reactants. Within the hydrogen partial pressures as defined no more hydrogen than necessary to hydrogenate the highly unsaturated compounds (olefins and/or dienes) is employed, since the excess hydrogen is usually vented. This preferably is a hydrogen partial pressure in the range of about 0.1 to 10 psia and even more preferably no more than 7 psia. optimal results have been obtained in the range between 0.5 and 5 psig hydrogen partial pressure. The hydrogen rates to the distillation column reactor are preferably maintained at between 5 and 40 SCFH.

In the drawings, such conventional items as reboiler, condensers, valves, and the like have been omitted, however those in the art and familiar with the principals of engineering will be readily able to recognize the placement of such items.

Referring now to the figure the process scheme may be more clearly seen. The hydrotreating zone 12 contains the non-acidic hydrotreating catalyst in the form of a catalytic distillation structure. The mixed aromatic feed is introduced via flow line 1 and some enters the hydrotreating zone 12. Hydrogen is fed below the hydrotreating zone 12 via flow line 2. The $C_9$ and heavier material is taken as bottoms via flow line 3. The feed is boiled up into the hydrotreating zone where substantially all of the olefins contained in the feed or produced in the isomerization reactor 11 are saturated. The catalysts in the hydrogenation zone is prepared as distillation structures.

All of the $C_8$ and lighter products are taken as overheads 6 from which the hydrogen and any $C_7$ lighter may be separated (not shown) with the hydrogen recycled to the reactor. The now hydrotreated mixed aromatic stream is then fed via flow line 8 or 8' to the selective adsorption units 20 or 20' where it is contacted with a molecular sieve 13 or 13' and the p-xylene depleted raffinate is removed via flow line 5 or 5', from whence it may be recovered or recycled back to the isomerization reactor for further p-xylene production.

The adsorption section comprises two adsorption units 20 and 20' are employed in parallel so that one unit may be in the desorption mode while the other is in the adsorption mode. The desorption solvent, e.g. toluene, is passed to the off-line reactor via line 7 or 7' to desorb the p-xylene, which is recovered via line 4 or 4'.

The isomerization reactor is operated as a separate conventional fixed bed straight pass unit 30. The catalyst may be in a continuous bed, tubes or even in the distillation packing, which provide a good flow structure, which is easy to handle and load into a continuous bed reactor. The raffinate from the adsorption section passing to unit 30 via line 9. Hydrogen for activation of the catalyst is conveniently added via line 2' into the feed to the reactor. The isomerate from unit 30 may be passed back to the column 10 via line 14 or to the adsorption section via line 15.

EXAMPLE

A xylene concentrate feed, contaminated with olefins was treated in a catalytic distillation column containing 450 grams of an alumina supported Pd hydrogenation catalyst deposited in pockets on a fiber glass wrapped into a bale with demister wire and disposed along a 20 foot 1" column. The xylene concentrate was feed to the mid point of the column at 2 pounds per hour. Hydrogen was fed to the bottom of the column at 0.5 to 1 SCFH over the run. Over a run of 207 hours the pressure was varied from 50–100 psig, bottoms temperature varied from 510°–530° F., catalyst zone from 440–470 and overhead was 440° F. The distillation split was 50% overhead, 50% bottoms and reflux varied from 5–10 to 1.

In the TABLE the operation of the column is shown by reference to the stream number in figure. The olefins in the overheads are substantially reduced.

TABLE

|  | STREAM #1 | | STREAM #3 | STREAM #6 |
| --- | --- | --- | --- | --- |
| HOURS ON STREAM | 189 | 213 | 213 | 207 |
| COMPONENTS, WT % | | | | |
| LIGHTS | 1.700 | 1.132 | 0.636 | 1.828 |
| BENZENE | 0.056 | 0.070 | 0.068 | 0.081 |
| TOLUENE | 0.408 | 0.394 | 0.119 | 0.689 |
| ETHYLBENZENE | 6.222 | 6.096 | 3.078 | 9.590 |
| PARA-XYLENE | 9.180 | 9.009 | 4.785 | 13.913 |
| META-XYLENE | 20.291 | 19.942 | 10.621 | 30.668 |
| CUMENE | 0.327 | 0.325 | 0.264 | 0.410 |
| ORTHO-XYLENE | 10.383 | 10.245 | 6.380 | 14.803 |
| HEAVIES | 51.434 | 52.788 | 74.050 | 28.018 |
| TOTAL | | | | |
| TOTAL XYLENE | 39.853 | 39.196 | 21.786 | 59.384 |
| BROMINE INDEX | ≈400 | ≈400 | 414.000 | 10.000 |

The invention claimed is:

1. A process for the production and recovery of para-xylene comprising the steps of:

(a) feeding hydrogen and a mixed aromatic stream containing para, meta and ortho-xylenes and olefins to a distillation column reactor having a reaction distillation zone containing a non-acidic hydrotreating catalyst in the form of a catalytic distillation structure;

(b) concurrently in said first reaction distillation zone
  (i) contacting the mixed aromatic stream with the hydrogen in the presence of the non-acidic hydrotreating catalyst to selectively hydrogenate substantially all of the olefins contained therein while maintaining the conditions in said first distillation reaction zone such that the reaction mixture is boiling and there is a continual internal reflux of $C_8$ and lighter material, and
  (ii) separating $C_8$ and lighter boiling material from the $C_9$ and heavier material;

(c) removing the $C_8$ and lighter material from said distillation column reactor as overheads;

(d) removing the $C_9$ and heavier material from said distillation column reactor as bottoms; and (e) feeding the $C_8$ and lighter material to a selective adsorption unit wherein the para-xylene is separated from the remainder of the $C_8$ and lighter material.

2. The process according to claim 1 comprising:
(d) feeding a para-xylene depleted material from the selective adsorption unit to an isomerization unit wherein additional para-xylene is produced; and
(e) feeding the effluent from said isomerization unit to said selective adsorption unit.

3. The process according to claim 1 wherein a portion of the effluent from said isomerization is fed to said distillation column reactor before feeding it to the selective adsorption unit.

4. The process according to claim 1 wherein said non-acidic hydrotreating catalyst comprises a Group VIII metal supported on an alumina base.

5. The process according to claim 1 wherein said selective adsorption unit contains an adsorbent selected from the group of type X and type Y structured zeolite.

6. The process according to claim 1 wherein hydrogen is added to said isomerization unit.

7. The process according to claim 1 wherein said non-acidic hydrotreating catalyst comprises a Group VIII metal supported on an alumina base.

8. The process according to claim 7 wherein said isomerization catalyst comprises a Group VIII metal containing zeolite.

9. The process according to claim 8 wherein said selective adsorption unit contains an adsorbent selected from the group of type X and type Y structured zeolite.

10. The process according to claim 1 wherein said aromatic stream contains about 50.0% m-xylene, 20.0% p-xylene, 20.0% o-xylene and 10.0% ethylbenzene.

11. The process according to claim 1 wherein said aromatic stream contains less than 1.0 wppm olefins.

12. The process according to claim 2 wherein said isomerization unit comprises a straight pass fixed bed unit.

13. A process for the production and recovery of para-xylene comprising the steps of:
(a) feeding to distillation reaction column:
  (i) hydrogen; and
  (ii) a mixed aromatic stream containing $C_8$ and lighter boiling material and $C_9$ and heavier boiling material comprising para, meta and ortho-xylenes, and olefins to a distillation column reactor having a reaction distillation zone containing a non-acidic hydrotreating catalyst in the form of a catalytic distillation structure;

(b) concurrently in said distillation column reactor:
  (i) boiling the mixed aromatic stream upward into the reaction zone with the hydrogen in the presence of the non-acidic hydrotreating catalyst in the distillation reaction zone to selectively hydrogenate substantially all of the olefins contained therein while maintaining the conditions in said first distillation reaction zone such that the reaction mixture is boiling and there is a continual internal reflux of $C_8$ and lighter material; and
  (ii) separating the $C_8$ and lighter boiling material from the $C_9$ and heavier material;

(c) removing the $C_8$ and lighter material from said distillation column reactor as overheads;

(d) removing the $C_9$ and heavier material from said distillation column reactor as bottoms; and (e) feeding the $C_8$ and lighter material to a selective adsorption unit wherein the para-xylene is separated from the remainder of the $C_8$ and lighter material; and (f) feeding a para-xylene depleted material from the selective adsorption unit to a fixed bed isomerization reactor containing an aromatic isomerization catalyst and contacting said para-xylene depleted stream with the aromatic isomerization catalyst in the presence of hydrogen to produce para-xylene.

\* \* \* \* \*